United States Patent [19]
Sekula et al.

[11] Patent Number: 5,516,544
[45] Date of Patent: May 14, 1996

[54] HIGH MOTECULAR WEIGHT LINKED ESTERIFIED PROPOXYLATED GLYCERINS USEFUL AS GELLING OR THICKENING AGENTS

[75] Inventors: Bernard C. Sekula, High Bridge, N.J.; Michael R. Ferenz, Coatesville, Pa.

[73] Assignees: ARCO Chemical Technology, L.P., Greenville, Del.; CPC International Inc., Englewood Cliffs, N.J.

[21] Appl. No.: 333,813

[22] Filed: Nov. 3, 1994

Related U.S. Application Data

[63] Continuation of Ser. No. 166,323, Dec. 10, 1993, Pat. No. 5,427,815.
[51] Int. Cl.[6] ........................ A23D 7/05
[52] U.S. Cl. .................. 426/611; 426/804; 536/18.3
[58] Field of Search .................. 426/611, 804; 536/18.3

[56] References Cited

U.S. PATENT DOCUMENTS

| | | | |
|---|---|---|---|
| 3,337,595 | 8/1967 | Lamont | 260/410.6 |
| 4,849,242 | 7/1989 | Kershner | 426/601 |
| 4,861,613 | 8/1989 | White et al. | 426/601 |
| 4,980,191 | 12/1990 | Christensen | 426/601 |
| 4,983,329 | 1/1991 | Cooper | 260/410.7 |
| 5,077,073 | 12/1991 | Ennis et al. | 426/531 |
| 5,118,448 | 6/1992 | Cooper | 554/168 |
| 5,135,683 | 8/1992 | Cooper | 554/151 |
| 5,137,743 | 8/1992 | Zaks et al. | 426/602 |
| 5,175,323 | 12/1992 | Cooper | 554/164 |
| 5,213,802 | 5/1993 | Masten | 424/439 |
| 5,219,604 | 6/1993 | Klemann et al. | 426/531 |
| 5,266,346 | 11/1993 | Klemann et al. | 426/611 |
| 5,354,573 | 10/1994 | Gross et al. | 426/603 |

FOREIGN PATENT DOCUMENTS

| | | |
|---|---|---|
| 415636A2 | 3/1991 | European Pat. Off. . |
| 433016A2 | 6/1991 | European Pat. Off. . |
| 0481717 | 4/1992 | European Pat. Off. . |
| 481523A1 | 4/1992 | European Pat. Off. . |
| 1595369 | 4/1970 | Germany . |
| 207070 | 2/1984 | Germany . |
| WO9201386 | 2/1992 | WIPO . |

OTHER PUBLICATIONS

Mitch: G et al. "Acabric Compounds with Fat–Like Functional Properties Die Nahrung", vol. 27, No. 9, pp. 853–876, 1983.
Aust. et al. "Orientational Studies On The Metabolism of Various Acaloric Compunds with Fat–Like Properties In The Ray". Die Nahrung vol. 32, No. 1, pp. 49–57, 1988.
Rizzi et al 1978 "A Solvent–free Synthesis of Sucrose Polyesters" JAOCS 55:398.
Markley 1961 Fatty Acids Part 2 Interscience Publishers Inc. N.Y. pp. 884–891.

*Primary Examiner*—Carolyn Paden
*Attorney, Agent, or Firm*—Stephen D. Harper

[57] ABSTRACT

Reduced calorie food compositions are prepared using linked esterified alkoxylated polyol fat substitutes comprised of polycarboxylate linking segments, polyol segments, and $C_6$–$C_{24}$ monocarboxylic fatty acid-esterified oxyalkylene segments, and, optionally, oxyalkylene segments between the polycarboxylate linking segments and the polyol segments. The fat substitutes are obtainable by alkoxylating a polyol such as glycerin with an epoxide such as propylene oxide and esterifying the resulting alkoxylated polyol with both a polycarboxylic acid or an equivalent thereof and a $C_6$–$C_{24}$ monocarboxylic fatty acid or an equivalent thereof, either simultaneously or sequentially.

8 Claims, 1 Drawing Sheet

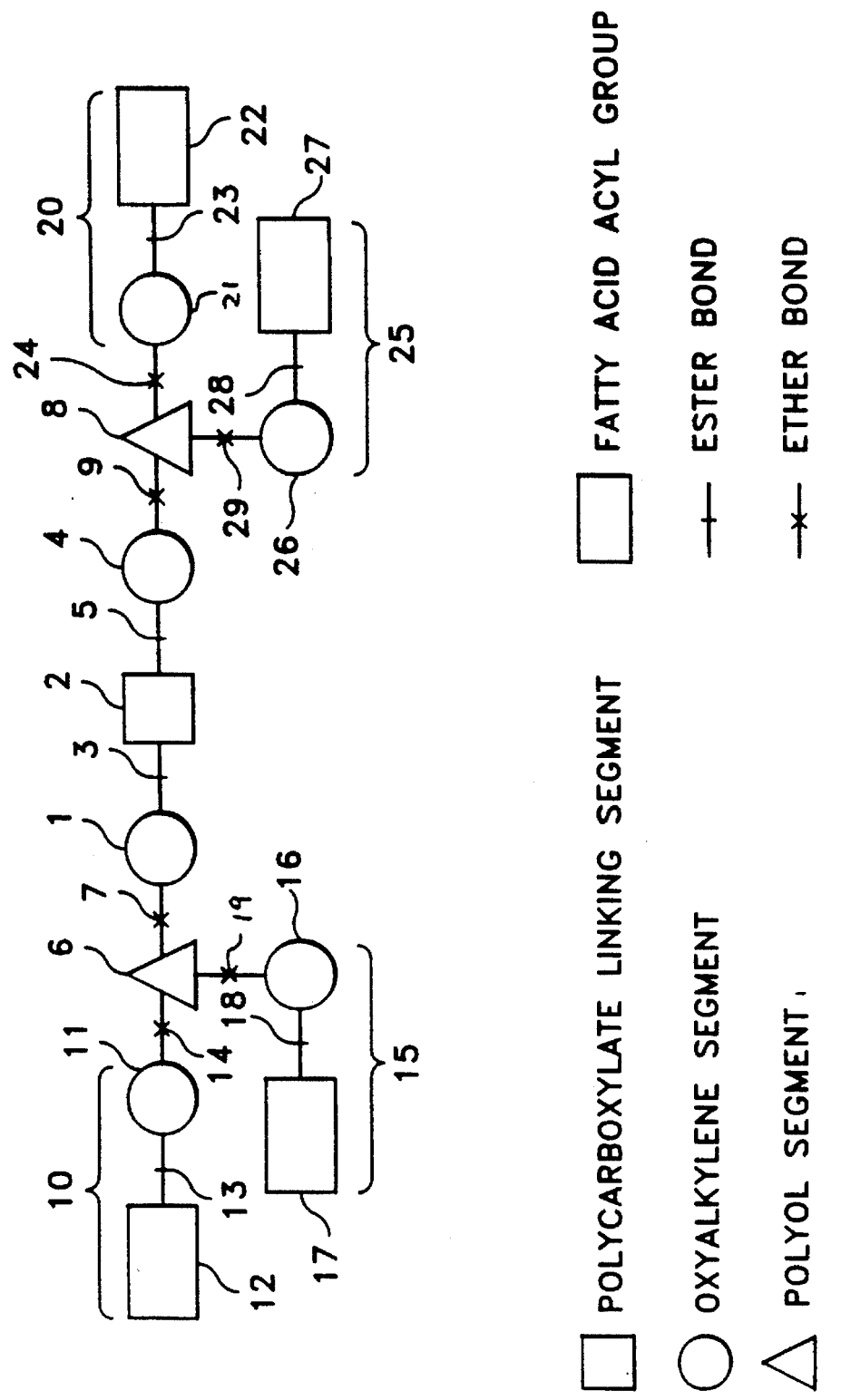

HIGH MOLECULAR WEIGHT LINKED ESTERIFIED PROPOXYLATED GLYCERINS USEFUL AS GELLING OR THICKENING AGENTS

This is a continuation, of application Ser. No. 08/166,323 filed on Dec. 10, 1993, now U.S. Pat. No. 5,427,815.

FIELD OF THE INVENTION

This invention relates to reduced calorie fat substitutes which are esterified alkoxylated polyols containing polycarboxylate linking segments. These fat mimetics are obtainable by esterifying an alkoxylated polyol such as propoxylated glycerin with at least one $C_6$–$C_{24}$ monocarboxylic acid entity such as a fatty acid and at least one polycarboxylic acid entity such as azelaic acid or a dimer fatty acid. The linked esterified alkoxylated polyols are useful as fully functional, replacements for edible lipids in the preparation of food compositions having significantly decreased caloric content. The fat substitutes contain a minimal number of hydrolyzable ester bonds as compared to analogous substances utilizing ester-bridged side chains.

BACKGROUND OF THE INVENTION

The consumption of high levels of triglyceride lipids has been associated with a number of health problems. Currently, obesity is one of the more prevalent metabolic problems among the general population. This condition in many people is attributed to the ingestion of a greater number of calories than is actually needed to supply energy for the maintenance and functioning of the body. Lipids are the most concentrated form of energy in the diet, with each gram of a triglyceride contributing about nine calories.

Maintaining a strict low fat diet, however, is difficult due to the fact that most people prefer the taste of "rich" foods, that is, foods that have the satisfying mouthfeel associated with fats and oils. In order for a reduced calorie food composition to adequately replace a conventional foodstuff, the fat substitute used in its preparation must mimic as closely as possible the organoleptic qualities of a triglyceride. The fat substitute must additionally have physical properties (viscosity, melting point, heat stability, thermal conductivity, etc.) resembling those of natural lipids since such properties often play a key role during preparation of a food composition. For example, in deep fat frying the oil acts as a heat transfer medium so as to impart crispness to the food being fried. At the same time, the ideal fat substitute should be non-toxic and should not cause any undesirable gastrointestinal side effects such as anal oil leakage, gas formation or diarrhea. This combination of attributes has in practice been quite difficult to achieve; the need to develop completely acceptable reduced calorie fat substitutes thus still exists.

U.S. Pat. No. 4,980,191 (Christensen) describes digestively hydrolyzable low calorie edible oil substitutes. The substitutes are esterified forms of polymerized $C_{18}$ unsaturated fatty acids that have the property of being at least partially hydrolyzed during digestion into simple alcohols and polybasic acids. Although the polybasic acids generated during digestion are higher in viscosity than the corresponding esters prior to hydrolysis, thus helping to avoid a laxative effect, these fat substitutes are not ideal since the alcohol portion does contribute calories to the diet. Moreover, the liberated alcohol may have other undesirable effects. For example, where ethyl esters are employed, as in the preferred embodiment of the described substitutes, the ethanol produced will act as an intoxicant. Other types of esters, such as methyl esters, may generate toxic alcohols when ingested.

U.S. Pat. No. 5,219,604 (Klemann et al.) teaches the use in fat substitutes of inter- and intramolecular ester bridges of the formula $-O-(CO)-(CH_2)_n-(CO)-O-$ where n is 1 to 8 formed by reacting dibasic acids with hydroxyl groups on the fatty side chains of fat compounds. Such fat substitutes, through the incorporation of hydroxy acids, thus inherently contain multiple ester linkages capable of being hydrolyzed upon ingestion. Where such hydrolysis takes place, the resulting hydrozylates are susceptible to further digestion; such fat substitutes may therefore have a higher level of available calories than otherwise would be desirable. Moreover, hydroxy fatty acids have certain deleterious physiological effects. The use of hydroxy fatty acids to prepare a fat substitute thus may not be desirable if digestion of the fat substitute will release such substances in the digestive tract.

U.S. Pat. No. 5,137,743 (Zaks et al.) describes the preparation of texturized oils and oil-continuous emulsions by combining liquid oils with minor amounts of certain high molecular weight polyester polymers. The polyester polymers include members of the class of polymers generally known as "alkyd" polymers, which are obtained by reaction of a polyhydric alcohol such as glycerol, a polybasic acid, and a fatty acid or oil. There is no suggestion, however, that the polyester polymers (which in the examples provided are in the form of powders) could be used by themselves at high levels as difficult to digest fat replacements in the preparation of reduced calorie food products.

SUMMARY OF THE INVENTION

This invention furnishes a reduced calorie fat substitute which is a linked esterified alkoxylated polyol comprised of at least one polycarboxylate linking segment, at least two polyol segments, and at least one $C_6$–$C_{24}$ monocarboxylic fatty acid-esterified oxyalkylene segment attached to a polyol segment, wherein each polyol segment is connected to a polycarboxylate linking segment either directly or through an oxyalkylene segment. Preferably, the polycarboxylate linking segment(s) has the general structure

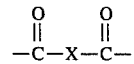

wherein X is an aliphatic moiety comprised of from 1 to 10 carbon atoms and up to 2 carbon-carbon double bonds or

wherein w is 2 or 3 and A represents the hydrocarbyl portion of a dimerized or trimerized fatty acid, the polyol segments have the general structure $R-(O-)_n$ wherein R is a $C_3$–$C_{12}$ hydrocarbyl group and n is an integer of from 3 to 8, the $C_6$–$C_{24}$ monocarboxylic acid-esterified oxyalkylene segment(s) has the general structure

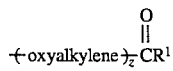

wherein oxyalkylene is oxyethylene, oxypropylene, or oxybutylene, Z is an integer of from 1 to 10, and $R^1$ is a $C_5$–$C_{23}$ hydrocarbyl group, and the optionally present oxyalkylene segment has the general structure -(oxyalkylene$^1$)$_y$ wherein oxyalkylene$^1$ is oxyethylene, oxypropylene, or oxybutylene and y is an integer of from 1 to 10. It is also highly desirable that the linked esterified alkoxylated polyol contain from 2 to 4 polyol segments and have a molecular weight of from 750 to 6000. Preferably, the number of $C_6$–$C_{24}$ monocarboxylic fatty acid-esterified segments is at least equal to the number of polyol segments.

The present invention also provides a linked esterified alkoxylated polyol useful as a reduced calorie fat substitute obtainable by esterification of an alkoxylated polyol with at least one $C_6$–$C_{24}$ monocarboxylic acid entity and at least one polycarboxylic acid entity. In a particularly preferred embodiment, the linked esterified alkoxylated polyol is obtainable by alkoxylation of a polyol having from 3 to 8 hydroxyl groups with from n to 10 n equivalents of a $C_2$–$C_6$ aliphatic epoxide, wherein n is equal to the number of hydroxyl groups on the polyol, to form an alkoxylated polyol and (b) esterification of the alkoxylated polyol with both (i) at least one $C_6$–$C_{24}$ monocarboxylic acid entity and (ii) a polycarboxylic acid entity selected from dimer or trimer fatty acid entities and dicarboxylic acid entities having the general structure $$\underset{\text{YCXCY}}{\overset{O\phantom{X}O}{\underset{\|\phantom{X}\|}{}}}$$

wherein X is is an aliphatic moiety comprised of from 1 to 10 carbon atoms and up to 2 carbon-carbon double bonds and Y is hydroxy, halide, or alkoxy, wherein the amount of $C_6$–$C_{24}$ monocarboxylic acid acid entity is from 1 to n–1 moles per mole of polyol and the amount of polycarboxylic acid entity is from 1/z to n–1/z moles per mole of polyol, where z is equal to the number of carboxylate functionalities in the polycarboxylic acid entity.

BRIEF DESCRIPTION OF THE DRAWING

FIG. 1 illustrates in schematic form an exemplary linked esterified alkoxylated polyol of this invention.

DETAILED DESCRIPTION OF THE INVENTION

The linked esterified alkoxylated polyol fat substitutes of this invention are organic compounds comprised of at least three types of covalently bonded moieties; namely, (1) polycarboxylate linking segments, (2) polyol segments, and (3) $C_6$–$C_{24}$ monocarboxylic fatty acid-esterified oxyalkylene segments. These moieties are connected to each other through either ether or ester bonds. Oxyalkylene segments not esterified with monocarboxylic fatty acid may optionally also be present. In a preferred embodiment, the total number of polycarboxylate linking segments, unesterified oxyalkylene segments, and $C_6$–$C_{24}$ monocarboxylic fatty acid-esterified oxyalkylene segments attached to each polyol segment is equal to the number of hydroxyl groups on the polyol from which said polyol segment is derived. However, it is also possible for a portion of the hydroxyl groups on the polyol to remain as free (unreacted) hydroxyl groups pendant to the polyol segment in the linked esterified alkoxylated polyol. Preferably, no more than one hydroxyl group is pendant to the polyol segment.

The polycarboxylate linking segments function so as to link together certain polyol segments within the fat substitute, either directly or through oxyalkylene segments, and are characterized by the presence of at least two carboxylate functionalities capable of forming ester bonds to said polyol or oxyalkylene segments. More than two carboxylate functionalities may also be present; di-, tri-, and tetracarboxylate linking segments are thus possible, for example. While the identity of the remainder of the polycarboxylate linking segment is not critical, it is generally preferred that it be aliphatic in character and not contain any aromatic, nitrogenous, or halogenated groups. Carbon-carbon double bonds or alicyclic groups may advantageously be present, however.

In one particular preferred embodiment, the polycarboxylate linking segment corresponds to the general structure $$\overset{O\phantom{XXX}O}{\underset{\|\phantom{XXX}\|}{-O-C-X-C-O-}}$$

wherein X is an aliphatic moiety comprised of from 1 to 10 carbon atoms and up to 2 carbon-carbon double bonds. For example, X may be $-(CH_2)_m-$ where m is an integer of from 1 to 10. Polycarboxylate linking segments of this type thus may be derived from dicarboxylic acids or their functional equivalents (halides, anhydrides, esters) such as, for example, malonic, succinic, glutaric, adipic, pimelic, suberic, azelaic, sebacic, undecanedioic, dodecanedioic, and brassylic acid and mixtures or combinations thereof. Branched, substituted (including hydroxy-substituted), or unsaturated di- and tri-carboxylic acid entities may also be utilized, including, without limitation, carboxystearic acid, polycarboxystearic acid, tricarballylic acid, aconitic acid, maleic acid, tartaric acid, citric acid, maleic acid, citraconic acid, cyclohexane dicarboxylic acid, ethyl malonic acid, methyl succinic acid, 2,2-dimethyl succinic acid, methyl glutaric acid, fumaric acid, methyl adipic acid, 2-ethyl-2-methyl succinic acid, diethyl malonic acid, tartaric acid, thapsic acid, dimethyl glutaric acid, cyclohexane diacetic acid, $C_{21}$ dicarboxylic acid (obtainable, for example, by reacting linoleic acid with acrylic acid), and their halides, anhydrides, esters and the like and mixtures thereof.

In another desirable embodiment, the polycarboxylate linking segment is derived from a dimer fatty acid, a trimer fatty acid, or a mixture of dimer and trimer fatty acids or their equivalents (halide, ester, anhydride). Such substances are well-known and are described, for example, in Leonard, "Dimer Acids", *Kirk-Othmer Encyclopedia of Chemical Technology*, 3rd Ed., Vol. 7, pp. 768–782 (1979), Leonard, *The Dimer Acids*, Humko Sheffield Chemical (1975), Johnson, "Dimerization and Polymerization", in E. H. Pryde, ed., *Fatty Acids*, American Oil Chemists' Society, pp. 343–352, (1979), and Pryde et al., "Aliphatic Dibasic Acids", in *Condensation Monomers*, Wiley-Interscience (1972). Especially preferred for use are the dimer and trimer fatty acids formed by the polymerization of $C_{18}$ unsaturated fatty acids such as oleic acid, linoleic acid, linolenic acid, elaidic acid and the like. The dimer fatty acid may have an acyclic, monocyclic, or bicyclic structure or comprise a mixture of compounds having different such structures. The use of a dimer or trimer fatty acid entity furnishes a polycarboxylate linking segment having the general structure $$\overset{O}{\underset{\|}{A-(C)_w}}$$

wherein w is 2 (as in a dimer acid) or 3 (as in a trimer acid) and A is the hydrocarbyl portion of a dimerized or trimerized fatty acid. Reference is made to FIG. 1 on page 348 of the Johnson publication referred to above, wherein examples of dimer structures are illustrated.

The oxyalkylene segments which may optionally be present in the fat substitute are interspersed between the polyol segments and the polycarboxylate linking segments, being connected to the former through ether bonds and to the latter through ester bonds. The oxyalkylene segments are not directly attached to a fatty monocarboxylic acid acyl group. Each oxyalkylene segment is comprised of one or more carbon-carbon-oxygen sequences, i.e.,

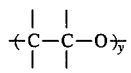

wherein y is at least 1 and preferably is not more than 10. An individual oxyalkylene segment may thus be monomeric or oligomeric in character and may be derived by ring-opening of an epoxide (a three membered cyclic ether). Especially preferred for use are $C_2$–$C_{10}$ aliphatic epoxides such as, for example, ethylene oxide, propylene oxide, 1,2-butene oxide, 2,3-butene oxide (cis and/or trans), isobutylene oxide, 1,2-pentene oxide, 2,3-pentene oxide, cyclopentene oxide, 1,2-hexene oxide, cyclohexene oxide, and the like and mixtures thereof. In certain embodiments of this invention, the use of $C_3$ and higher 1,2-alkylene oxides such as propylene oxide and 1,2-butene oxide is particularly desirable so as to create predominately secondary ester bonds between the terminus of the oxyalkylene segment and the polycarboxylate linking segment. It may in certain applications be advantageous to control the structure of the ester bonds such that at least 95% of such bonds are secondary and less than 5% of such bonds are primary. An oxyalkylene segment thus may have the general structure

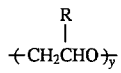

wherein R is hydrogen or $C_1$–$C_6$ alkyl (methyl, ethyl, cyclohexyl, and the like) and y is an integer of from 1 to 10. The value of y may, of course, vary between individual oxyalkylene segments within the same linked esterified alkoxylated polyol. An oxyalkylene segment may advantageously be comprised of different types of ring-opened epoxide units (for example, both oxyethylene and oxypropylene units) which are present in either a random or block configuration.

The $C_6$–$C_{24}$ monocarboxylic fatty acid-esterified oxyalkylene segments are attached to the polyol segments through ether bonds and are themselves individually comprised of both an oxyalkylene segment and a fatty acid acyl group. Said oxyalkylene segment may correspond in structure to the oxyalkylene segments described previously hereinabove (e.g., oxyethylene, polyoxyethylene, oxypropylene, polyoxypropylene, oxybutylene, polyoxybutylene, mixed polyoxyethylene/oxypropylene, preferably containing from 1 to 10 ring-opened epoxide units). The fatty acid acyl group, which is connected to the oxyalkylene segment of the $C_6$–$C_{24}$ monocarboxylic acid-esterified oxyalkylene segment by an ester bond, preferably has the general structure

wherein R is a $C_5$–$C_{23}$ hydrocarbyl group (linear or branched; saturated, monounsaturated, or polyunsaturated). The fatty acid acyl group is desirably derived from a monocarboxylic fatty acid or the equivalent thereof (halide, ester, anhydride). Such fatty acids and their equivalents are readily available at low cost from natural sources such as edible triglycerides. Specific illustrative fatty acids suitable for use include, but are not limited to, eicosanoic (arachidic) acid, heneicosanoic acid, docosanoic (behenic) acid, elaidic acid, tricosanoic acid, tetracosanoic (lignoceric) acid, caprylic acid, pelargonic acid, capric acid, caproic acid, lauric acid, palmitic acid, stearic acid, oleic acid, cetoleic acid, myristic acid, palmitoleic acid, gadoleic acid, erucic acid, rincinoleic acid, linoleic acid, linolenic acid, myristoleic acid, eleostearic acid, arachidonic acid, or mixtures or hydrogenated derivatives of these acids. The fatty acids may be derived synthetically or from natural sources such as triglyceride lipids. Mixtures of fatty acid entities, such as the mixtures of fatty acids typically obtained by hydrolysis (splitting) of a triglyceride such as corn oil or soybean oil, may advantageously be used.

The properties and characteristics of the linked esterified alkoxylated polyol may be varied or controlled as desired by adjusting the relative proportions of $C_6$–$C_{24}$ monocarboxylic fatty acid-esterified oxyalkylene segments to polycarboxylate linking segments. Decreasing the $C_6$–$C_{24}$ monocarboxylic fatty acid-esterified oxyalkylene segment: polycarboxylate segment molar ratio generally will increase the molecular weight of the linked esterified alkoxylated polyol, for example. The precise ratio selected for use is not critical and may vary within wide limits depending upon other factors such as, for example, the number of hydroxyl groups on the polyol and the number of carboxylate functionalities on the polycarboxylic acid entity. Where the polyol has three hydroxyl groups and the polycarboxylic acid entity is a dicarboxylic acid, for example, illustrative ratios which are suitable for use include 4:1, 5:2, 6:3, and 7:4.

The linked esterified alkoxylated polyols of this invention contain a minimum of two polyol segments, but may also contain three, four, or an even higher number of such segments. To limit viscosity, it will generally be desirable for the linked esterified alkoxylated polyol to contain no more than four polyol segments. Each polyol segment will correspond to the generic formula R–(O–)$_n$ and is derived from a polyol or a polyol equivalent wherein the polyol is a polyhydric alcohol containing three or more hydroxyl groups. R in the foregoing formula thus is an organic moiety such as a hydrocarbyl entity containing at least three carbon atoms, hydrogen, and, optionally, other elements such as oxygen or nitrogen; the polyol segments are connected to both oxyalkylene segments and $C_6$–$C_{24}$ monocarboxylic acid-esterified oxyalkylene segments through ether bonds. In preferred embodiments, the polyol segment does not contain any hydrolyzable ester groups. The number of hydroxyl groups on the polyol (n) is most suitably from 3 to 8. The polyol (which preferably contains primary and/or secondary hydroxyl groups) may be selected from $C_3$–$C_{12}$ aliphatic triols (e.g., glycerol, 1'2'4-butane triol, 2,3,4-pentane triol, 2-ethyl-2-(hydroxymethyl)-1,3-propane triol (trimethylol propane), 1,1,1-tris(hydroxymethyl)ethane, 1,2,6-trihydroxyhexane, 1,2,3-heptanetriol, and the like), $C_4$–$C_{12}$ aliphatic tetrols (eg., erthyritol, sorbitan, pentaerythritol), $C_5$–$C_8$ sugar alcohols [including those compounds corresponding to the formula $HOCH_2(CHOH)_nCH_2OH$ wherein n is 3 to 6 such as xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, lactose, maltose) and alkyl glycosides (e.g., methyl glycosides, ethyl glycosides, propyl glycosides, and other glycoside molecules wherein the alkyl glycoside is an acetal formed by interaction of a $C_1$-$C_{20}$ alcohol with a carbonyl group of a mono- or disaccharide such as glucose). Also suitable for use as the polyol are hydroxy-containing substances such as tetrahydrofuran oligomers, oxetane oligomers, glycerol oligomers, and the like.

segment could alternatively be connected to two oxyalkylene segments, which in turn are both attached to the same polyol segment. One or both of oxyalkylene segments 1 and 4 could be omitted, resulting in direct attachment of the polyol segments to the polycarboxylate linking segment.

The structure of a specific example of a linked esterified alkoxylated polyol within the class of fat substitutes embraced by the present invention may be represented as follows:

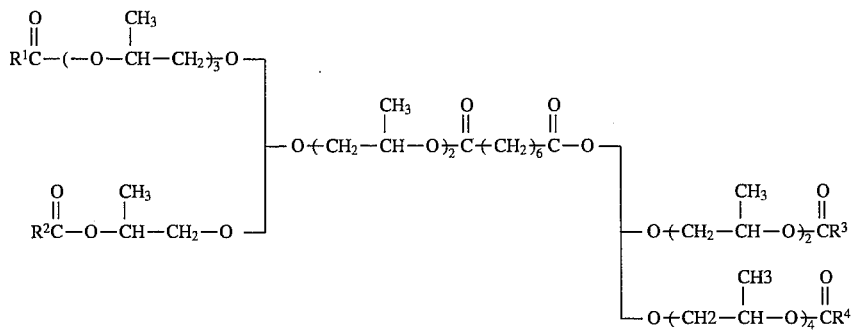

In a preferred embodiment, the polyol is glycerin so as to provide a polyol segment having the structure

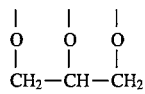

in the linked esterified alkoxylated polyol (i.e., $R=C_3H_5$ and $n=3$ in the foregoing formula). Glycerin may be readily and economically obtained by hydrolytic splitting of a natural triglyceride. The fatty acids obtained in such a splitting operation may also be utilized in the preparation of the linked esterified alkoxylated polyol.

To better illustrate the interrelationships between the different components of the linked esterified alkoxylated polyol fat substitute of this invention, an example of such a substance is diagrammed schematically in FIG. 1. In this illustrative example, oxyalkylene segment 1 is attached to polycarboxylate linking segment 2 by ester bond 3. Oxyalkylene segment 4 is also attached to 2 by ester bond 5. Polyol segment 6 is attached to 1 through ether bond 7, while polyol segment 8 is similarly attached to 4 through ether bond 9. $C_6$–$C_{24}$ monocarboxylic acid-esterified oxyalkylene segment 10, comprised of oxyalkylene segment 11 and fatty acid acyl group 12 joined by ester bond 13, are attached to 6 through ether bond 14. $C_6$–$C_{24}$ monocarboxylic acid-esterified oxyalkylene segment 15, comprised of oxyalkylene segment 16 and fatty acid acyl group 17 joined by ester bond 18, are attached to 6 through ether bond 19. $C_6$–$C_{24}$ monocarboxylic acid-esterified oxyalkylene segment 20, comprised of oxyalkylene segment 21 and fatty acid acyl group 22 joined by ester bond 23, are attached to 8 by ester bond 24. $C_6$–$C_{24}$ moncarboxylic acid-esterified oxyalkylene segment 25, comprised of oxyalkylene segment 26 and fatty acid acyl group 27 joined by ester bond 28, are attached to 8 through ether bond 29. Variations upon this structure will be readily apparent to the person of ordinary skill in the art familiar with the teachings of the instant specification. For example, $C_6$–$C_{24}$ monocarboxylic acid-esterified oxyalkylene segment 10 could be replaced by another polycarboxylate linking segment which is itself connected to additional oxyalkylene, polyol, and $C_6$–$C_{24}$ monocarboxylic acid-esterified oxyalkylene segments. A polycarboxylate linking wherein $R^1$ is –$(CH_2)_{16}CH_3$, $R^2$ and $R^4$ are –$(CH_2$––$)_7CH=CH$ –$(CH_2)_7CH_3$ and $R^3$ is –$(CH_2)_{20}CH_3$.

To minimize direct absorption of the fat substitute through the walls of the gastrointestinal tract, it is highly advantageous for the molecular weight of the linked esterified alkoxylated polyol to be at least 750 (more preferably, at least 900). To avoid undesirably high viscosities, the molecular weight generally should be no greater than 6000 and preferably is 3000 or less. It will be particularly advantageous (where the linked esterified alkoxylated polyol is to be used to replace most or all of the triglyceride portion of a food composition) to control the molecular weight, degree of cross-linking, and other structural parameters such that the viscosity of the linked esterified alkoxylated polyol is less than 1000 cps (more preferably less than 500 cps; most preferably, less than 250 cps) as measured by Brookfield viscometer at 100° F. (38° C.).

The higher molecular weight linked esterified alkolylated polyols, while perhaps too viscous to be easily used alone as 100% replacements for triglycerides in the fat component of a food composition, may be advantageously blended with low viscosity digestible triglycerides or non-linked esterified alkoxylated polyols (or other fat substitutes such as sucrose polyester). Such linked esterified alkoxylated polyols may beneficially act as gelling or thickening agents. For example, when combined at the 0.5 to 25 weight % level with liquid unsaturated triglycerides, higher molecular weight linked esterified alkoxylated polyol in accordance with the invention may modify the viscosity or melting properties of such triglycerides such that they closely resemble those of solid or semi-solid fats containing high levels of saturated fatty acids. Alternatively, the tendency of a liquid fat substitute such as certain non-linked esterified alkoxylated polyols to exhibit anal oil leakage when consumed in large quantities may be effectively suppressed by incorporation of the linked esterified alkoxylated polyol. Reduced calorie fat substitutes comprised of liquid triglycerides, liquid non-linked esterified alkoxylated polyols, and higher molecular weight linked esterified alkoxylated polyols may also provide certain advantages (e.g. reduced anal oil leakage as compared to analogous compositions not containing the linked esterified alkoxylated polyol).

The linked esterified alkoxylated polyol fat substitutes will deliver less than 9 Kcal/gram, preferably less than 5

Kcal/gram, and, in some embodiments, less than 3 Kcal/gram, upon being metabolized by the human body. Where a maximum reduction in the caloric content of a food composition is desired, the linked esterified alkoxylated polyol may be selected such that it delivers essentially 0 Kcal/gram when consumed.

In preferred embodiments of the invention, the structures of the various ester bonds incorporated in the linked esterified alkoxylated polyol are controlled such that differential reactivity with respect to hydrolytic cleavage by digestive enzymes such as lipase is attained. This results not only in a reduction in effective caloric value as compared to a triglyceride, but also the selective conversion of the fat substitute to a product or intermediate which is less oil-like in nature. The product of such a controlled digestive process may have decreased hydrophobicity, and thus greater hydrophilicity, relative to the parent linked esterified alkoxylated polyol. Such a product of a process of controlled digestion will tend to have not only decreased oiliness, but may also function as a emulsifier or surface active agent capable of emulsifying any undigested fat substitute or oil-like digestive by products. Thus, the fat substitutes of this invention can be selected such that they will resemble natural lipids (triglycerides) in taste and texture when consumed, yet be less prone to exit the gastrointestinal tract as a persistent oil compared to certain substances taught as fat substitutes in the prior art.

One method by which the relative digestibility of the linked esterified alkoxylated polyol may be adjusted as may be desired for a particular application is to vary the extent of steric hinderance present at the ester linkage. For example, bulky substitutents may be introduced on the carbon atoms adjacent to the ester oxygen atom or the ester carbonyl carbon atom so as to block or interfere with the ability of the ester linkage to closely associate with the active sites on the lipase enzymes responsible for catalyzing ester hydrolysis.

The linked esterified alkoxylated polyols of this invention may be prepared by adaptation of conventional alkoxylation and esterification techniques. For example, a polyol may be reacted with the desired number of equivalents of an epoxide in the presence of an appropriate catalyst (e.g., alkali metal) so as to ring-open the epoxide and to add oxyalkylene segments onto the hydroxyl groups of the polyol to form an alkoxylated polyol. The alkoxylated polyol may then be reacted, either simultaneously or sequentially, with the desired combination and proportions of both a monocarboxylic fatty acid (or an anhydride, ester, or halide thereof) or mixture of monocarboxylic fatty acids and a polycarboxylic acid entity (free acid, anhydride, ester, or halide) or mixture of polycarboxylic acid entities so as to generate the linked esterified alkoxylated polyol. Direct esterification (i.e., with free fatty acids, either self-catalyzed or with a suitable catalyst), transesterification (i.e., with methyl esters or the like, with or without catalyst), and interesterification methods may all be employed, together with other known procedures for forming ester bonds. Such procedures are described, for example, in Markley, "Esters and Esterification", in *Fatty Acids,* Markley, ed., Second Edition Part 2, Chapter IX, pp. 757–984 (1961). An alternative approach is to simultaneously react epoxide, polyol, and a triglyceride (a fatty acid triester of glycerin) in the presence of base or other suitable catalyst to form a partially esterified alkoxylated polyol and to thereafter react with the desired amount of polycarboxylic acid entity so as to generate polycarboxylate linking segments.

To prepare linked esterified alkoxylated polyols wherein the polycarboxylate linking segments are attached directly to polyol segments without intervening oxyalkylene segments, alkoxylated polyols containing protective groups may be used. Such protective groups (e.g., acetals, ketals, tertiary alkyl groups, tetrahydropyranyl groups, triphenylmethyl groups, benzyl groups) are placed on a portion of the hydroxyl groups of the polyol prior to alkoxylation, then removed prior to esterification. U.S. Pat. Nos. 5,118,448 and 5,135,683 describe methods for obtaining and reacting such alkoxylated polyols which may be readily adapted for use in synthesizing linked esterified alkoxylated polyol fat substitutes of this type.

The relative molar proportions of $C_6$–$C_{24}$ monocarboxylic acid entity and polycarboxylic acid entity utilized may be varied within wide limits to attain the desired ratio of $C_6$–$C_{24}$ monocarboxylic fatty acid-esterified oxyalkylene segments to polycarboxylate linking segments in the linked esterified alkoxylated polyol. For example, it will typically be desirable for the amount of monocarboxylic fatty acid reacted to be from 1 to n–1 moles per mole of polyol and the amount of polycarboxylic acid to be from 1/z to n–1/z moles per mole of polyol where n is equal to the number of hydroxyl groups on the polyol and z is equal to the number of carboxylate functionalities in the polycarboxylic acid entity. In the embodiment of this invention wherein the polyol is a triol such as glycerin, the polycarboxylic acid entity is a dicarboxylic acid entity, and an average of from 2 to 4 polyol segments per molecule of the linked esterified alkoxylated polyol is desired, the amount of the dicarboxylic acid entity reacted per mole of polyol should be from 0.5 to 0.75 moles. In another embodiment, substantially all of the available hydroxyl groups are esterified (either with monocarboxylic fatty acid or polycarboxylic acid) such that the total of the number of moles of monocarboxylic fatty acid plus z times the number of moles of polycarboxylic acid is equal to or nearly equal to n times the number of moles of polyol. Incompletely esterified substances will also be suitable for use, however, provided they exhibit physical and organoleptic properties resembling natural fats and oils.

A reduced calorie fat substitute produced by the procedures described hereinabove may be additionally purified or treated so as to render it more suitable for use in food compositions using any of the techniques known in the art for refining natural vegetable or animal lipids. Such techniques include, but are not limited to, degumming, bleaching, filtration, deodorization, hydrogenation, dewaxing, and the like. Various additives such as stabilizers, anti-oxidants (e.g., tocopherols, hindered phenols such as BHT, hydroquinones such as TBHQ), vitamins (e.g., fat-soluble vitamins such as vitamin A, D, E, and K) and so forth can also be incorporated into the linked esterified alkoxylated polyol.

It should be understood that by the nature of the reactions taking place as described hereinabove during the preparation of the linked esterified alkoxylated polyols, the compositions obtained will generally be mixtures of individual compounds which have a range of molecular weight and which may contain different structural isomers. Also, depending upon the synthetic procedure used, minor amounts of other materials such as non-linked esterified alkoxylated polyols may be generated together with the linked esterified alkoxylated polyols of this invention. The use of such mixed reaction products as fat substitutes may be advantageous under certain circumstances. For example, the presence of non-linked esterified alkoxylated polyol may beneficially lower the viscosity, hardness or melting point of a linked esterified alkoxylated polyol. Non-linked esterified alkoxylated polyols of the type described in U.S. Pat. Nos. 4,861,613, 5,509,443, 5,077,073, and 4,980,191 and European Pat. Publication No. 481,523 (incorporated herein by reference in their entirety) may also be deliberately blended in any proportion (e.g., 1:99 to 99:1) with the linked esterified alkoxylated polyols of this invention to provide reduced calorie fat substitutes.

The linked esterified alkoxylated polyols of this invention may be used as partial or total (100%) replacements for conventional lipids in any edible fat-containing food composition. The amount of the fat mimetic employed is sufficient to effectively reduce the available calories of the food composition as compared to a food composition prepared using an equivalent amount (weight or volume) of a conventional fully digestible triglyceride lipid alone. Preferably, at least about 10 percent (more preferably, at least about 25 percent by weight) of the total fat component of the food composition is comprised of the linked esterified alkoxylated polyol.

The triglyceride lipid admixed with the linked esterified propoxylated glycerin composition may be any of the known edible fatty acid triglycerides available from natural or synthetic sources. These edible fatty acid triglycerides include, but are not limited to, fats and oils such as tallow, soybean oil, cottonseed oil, coconut oil, palm kernel oil, corn oil, fish oil, lard, butterfat, olive oil, palm oil, peanut oil, safflower seed oil, cocoa butter, sesame seed oil, rapeseed oil, sunflower seed oil, as well as fully or partially hydrogenated derivatives and mixtures of these triglycerides. While the linked esterified alkoxylated polyol composition may be combined in any proportion with the triglyceride lipid, weight ratios of from 5:95 to 95:5 are particularly advantageous. The triglyceride lipid may be selected so as to impart a desirable caloric content, flavor, aroma, mouth feel, thermal stability, viscosity, rheology (Newtonian or non-Newtonian) or other property to the blend and to the final food composition.

The physical, organoleptic, and physiological properties and characteristics of the linked esterified alkoxylated polyols of this invention may be controlled as desired by varying the identities and relative proportions of the polyols, epoxides, polycarboxylic acids, and $C_6$–$C_{24}$ monocarboxylic fatty acids incorporated therein. The composition of the alkoxylated polyols may thus be readily altered so as to render the fat substitute completely liquid, completely solid, or partially liquid and partially solid at room temperature (i.e., the solid fat index may range from 0 to 100%).

In certain embodiments of the invention (for example, where the linked esterified alkoxylated polyol comprises at least 50% by weight of the fat component present in a food product), the linked esterified alkoxylated polyol preferably has a solid fat index as measured by dilatometry of from 0 to a maximum of 50 at body temperature (37° C.) to provide a pleasant creamy or smooth (i.e., non-waxy) consistency and texture in the food product.

The fat substitute of this invention can replace, in full or in part, a triglyceride lipid in a cooking oil, frying oil, salad oil, or shortening, for example. Additional uses include combining the linked esterified alkoxylated polyol with other foodstuff ingredients to form food compositions such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies and confectioneries (especially those normally containing fatty ingredients such as chocolate or peanut butter), soups, and dry baking mixes (for muffins, cakes, pancakes, waffles, brownies, and the like). Owing to the fat-like properties and stability of the linked esterified alkoxylated polyols, minimum reformulation of standard food compositions will generally be required. The viscosity, melting profile, yield point, hardness, thixotropic area, liquid/solid stability, solid fat index, rheology, plasticity, and other physical properties of the linked esterified alkoxylated polyol are preferably selected such that they mimic as closely as possible the analogous properties of the conventional triglyceride being replaced.

Illustrative ingredients (including both fatty food ingredients and non-fat food ingredients) which may be used in combination with the fat mimetics of this invention include carbohydrates (flour, starches, sugars, celluloses), edible lipids (triglycerides), proteins (from animal or vegetable sources), vitamins (including, but not limited to, fat soluble vitamins such as vitamin A, vitamin D, vitamin E, and vitamin K), antioxidants, emulsifiers (including, but not limited to, the emulsifiers listed as approved for food use in the United States Code of Federal Regulations), thickeners, preservatives, colorants, flavors, fragrances, sugar substitutes (saccharin, aspartame, sucralose, cyclamates, and the like), other fat substitutes or fat mimetics (for example, polyol polyesters such as sorbitol polyesters and sucrose polyesters, non-linked esterified alkoxylated polyols such as esterified propoxylated glycerin, or caprenin), bulking agents such as polydextrose, dietary fibers, water, milk, spices, eggs, and the like. Oil-in-water or water-in-oil emulsions can be readily prepared by combining water, the linked esterified alkoxylated polyol, and other ingredients such as emulsifiers. The linked esterified alkoxylated polyols of this invention are particularly suitable for the preparation of food compositions requiring exposure to elevated temperatures. Unlike other proposed fat substitutes such as proteinacious macrocolloids or certain polysaccharide-based substances requiring water to render them fat-like in texture, the fat mimetics of this invention are thermally stable and do not readily decompose or lose their fat-like properties when heated. The fat mimetics thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crisping).

From the foregoing description, one skilled in the art can readily ascertain the essential characteristics of this invention and, without departing from the spirit and scope thereof, make various changes and modifications to the invention to adapt it to various usages, conditions, and embodiments.

The following examples further illustrate the compositions of this invention, but are not limitative of the invention in any manner whatsoever.

EXAMPLE 1

This example demonstrates the preparation of a linked esterified alkoxylated polyol in accordance with the invention. A propoxylated glycerin (324.4 parts by weight) prepared by reacting 4 equivalents of propylene oxide with 1 equivalent of glycerin in the presence of a potassium catalyst is treated with magnesium silicate to remove residual catalyst, combined with stearic acid (569.0 parts) and tin (II) chloride (5.4 parts), then heated under vacuum (10 torr) at 150° C. with nitrogen sparging until at least 95% conversion of the stearic acid has occurred. Adipic acid (73.1 parts) is then added and heating continued at a vacuum of 100 mm until at least 95% conversion of the hydroxyl groups of the initial propoxylated glycerin has been attained. Any unreacted adipic acid taken overhead is recycled. Catalyst is removed by washing the reaction product five times with an equal volume of water, heating the washed product with magnesium silicate (5% by weight) for 2 hours at 90° C., and filtering. The filtered product is steam stripped under 10 mm Hg pressure until the residual acidity is less than 1 mg KOH/gram. The purified linked esterified alkoxylated polyol thereby obtained is useful as a fat substitute in the preparation of reduced calorie food products.

EXAMPLE 2

The procedure of Example 1 is repeated using oleic acid (564.9 parts) instead of stearic acid and brassylic acid (122.2 parts) instead of adipic acid. The oleic acid and brassylic acid are reacted simultaneously with the propoxylated glycerin at a temperature of 125° C. and a vacuum of 10 mm Hg until greater than 95% esterification of the hydroxy groups of the propoxylated glycerin is achieved. The expected product is a linked esterified alkoxylated polyol suitable for use in reducing the caloric content of a fat component-containing food product.

EXAMPLES 3–11

These examples demonstrate the preparation of linked esterified alkoxylated polyol fat substitutes within the scope of this invention using different alkoxylated polyols, $C_6$–$C_{24}$ monocarboxylic acid entities, and polycarboxylic acid entities in varying proportions. The reactants listed in Table I are reacted using conditions similar to those described in Example 1, except that in Examples 3–5 the potassium catalyst used to prepare the alkoxylated polyol is not removed prior to the esterification steps. The desired esterification is catalyzed by the residual potassium catalyst in the alkoxylated polyol; the tin (II) chloride is omitted and the reactants heated at 200° C. and a pressure of 10 mm Hg (to remove the methanol co-product generated during transesterification) until at least 95% conversion of both the $C_6$–$C_{24}$ monocarboxylic acid and the hydroxyl groups of the initial alkoxylated polyol is achieved. Following purification, a linked esterified alkoxylated polyol useful as a reduced calorie replacement for digestible triglycerides in food compositions is expected to be obtained in each example.

TABLE I

| Example No. | Epoxide | Polyol | Epoxide:Polyol molar ratio | $C_6$–$C_{24}$ Monocarboxylic Acid Entity | Polycarboxylic Acid Entity | Molar Ratio Alkoxylated Polyol:Fatty Acid:Polycarboxylic Acid |
|---|---|---|---|---|---|---|
| 3 | ethylene oxide | trimethylol propane | 6:1 | soybean oil fatty acid methyl esters | e | 2:3.22:1 |
| 4 | 1,2-butene oxide | 1,2,6-hexane triol | 10:1 | partially hydrogenated soybean oil fatty acid methyl esters (iodine value = 30) | f | 1.3:1.91:1 |
| 5 | a | diglycerol | 12:1 | fully hydrogenated high erucic rapeseed oil fatty acid methyl esters | g | 2:5.98:1 |
| 6 | b | pentaerythritol | 8:1 | corn oil fatty acids | pimelic acid | 3:8:2 |
| 7 | propylene oxide | sucrose | 8:1[d] | cottonseed oil fatty acids | azelaic acid | 2:14:1 |
| 8 | c | sorbitol | 18.1 | beef tallow fatty acids | sebacic acid | 4:18:3 |
| 9 | ethyl glycidyl ether | methyl glucoside | 10:1 | coconut oil fatty acids | dodecanedioic acid | 2:3:1 |
| 10 | 1,2-hexene oxide | 2,3,4,5-hexane tetrol | 5:1 | 2:1 (by weight) blend of fully hydrogenated high erucic rapeseed oil fatty acids and peanut oil fatty acids | $C_{21}$ dicarboxylic acid (from linoleic acid) | 4:10:3 |
| 11 | propylene oxide | xylitol | 20:1 | canola oil fatty acids | carboxystearic acid ($C_{19}$ dicarboxylic acid) | 2:8:1 | a. mixture of ethylene oxide and propylene oxide (equimolar amounts)
b. mixture of propylene oxide and 1,2-butene oxide (molar ratio 3:1)
c. ethylene oxide (528 parts) reacted first with the sorbitol (182 parts), followed by propylene oxide (348 parts)
d. prepared in accordance with the procedures described in U.S. Pat. No. 2,908,681 (Anderson et al.)
e. methyl esters of polymerized $C_{18}$ fatty acids comprised of 2% mono-basic acid, 18% dibasic acid (dimer), and 80% tribasic acid (trimer), prepared in accordance with U.S. Pat. No. 4,980,191 (Christensen)
f. methyl esters of polymerized $C_{18}$ fatty acids comprised of 3% monobasic acid, 35% dibasic acid (dimer), and 62% tribasic acid (trimer) ester, prepared in accordance with U.S. Pat. No. 4,980,191 (Christensen)
g. methyl ester of polymerized $C_{18}$ fatty acids comprised of 1% monobasic acid, 96% dibasic acid (dimer), and 3% tribasic acid (trimer) esters, prepared in accordance with U.S. Pat. No. 4,980,191 (Christensen)

EXAMPLE 12

This example demonstrates the utility of the linked esterified alkoxylated polyols of this invention in the formulation of food products having significantly reduced caloric content as compared to analogous products prepared using natural triglycerides (i.e., vegetable oils) exclusively.

A vanilla-flavored frozen dessert is prepared by mixing 10X sugar (15.0 parts by weight), non-fat dry milk (3.9 parts), and salt (0.4 parts) into water (39.0 parts) for 3 minutes. The linked esterified alkoxylated polyol of Example 1 (28.4 parts) is then added in liquid form and the resulting mixture cooked to 200° F. while stirring. The mixture is cooled to 160° F. Sugared egg yolks (12.5 parts) and vanilla extract (0.8 parts) are added and mixed well. The resulting product is cooled and then frozen to yield the vanilla-flavored frozen dessert.

We claim:

1. A composition useful as a reduced calorie fat substitute comprising:
   (a) a liquid non-linked esterified propoxylated glycerin; and
   (b) a linked esterified propoxylated glycerin comprised of:
      (i) at least two polycarbonyl linking segments;
      (ii) at least three glyceryl segments; and
      (iii) at least one $C_6$–$C_{24}$ monocarboxylic fatty-acid esterified oxypropylene segment attached to a glyceryl segment;
   wherein each glyceryl segment is connected to a polycarbonyl linking segment either directly or through an oxypropylene segment and the linked esterified propoxylated glycerin has a molecular weight greater than 6000.

2. The composition of claim 1 wherein the proportion of liquid non-linked esterified propoxylated glycerin to linked esterified propoxylated glycerin is from 1:99 to 99:1.

3. The composition of claim 1 additionally comprising a liquid triglyceride.

4. The composition of claim 1 wherein the linked esterified propoxylated glycerin has a viscosity of greater than 1000 cps as measured by Brookfield viscometer at 100° F.

5. The composition of claim 1 wherein the polycarbonyl linking segments have the general structure

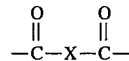

wherein X is an aliphatic moiety comprised of 1 to 10 carbon atoms and up to 2 carbon-carbon double bonds.

6. The composition of claim 1 wherein the polycarbonyl linking segments have the general structure

wherein w is 2 or 3 and A represents the hydrocarbyl portion of a dimerized or trimerized fatty acid.

7. The composition of claim 1 wherein the $C_6$–$C_{24}$ monocarboxylic fatty acid-esterified oxypropylene segment has the general structure

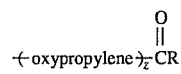

wherein z is an integer of from 1 to 10 and R is a $C_5$–$C_{23}$ hydrocarbyl group.

8. A method of suppressing the tendency of a liquid non-linked esterified propoxylated glycerin fat substitute to exhibit anal oil leakage when consumed comprising incorporating into said liquid non-linked esterified propoxylated glycerin fat substitute a linked esterified propoxylated glycerin comprised of:
   (a) at least two polycarbonyl linking segments;
   (b) at least three glyceryl segments; and
   (c) at least one $C_6$–$C_{24}$ monocarboxylic fatty acid esterified oxypropylene segment attached to a glyceryl segment, wherein each glyceryl segment is connected to a polycarbonyl linking segment either directly or through an oxypropylene segment and the linked esterified propoxylated glycerin has a molecular weight greater than 6000.

* * * * *

UNITED STATES PATENT AND TRADEMARK OFFICE
CERTIFICATE OF CORRECTION

PATENT NO. : 5,516,544
DATED : May 14, 1996
INVENTOR(S) : Bernard C. Sekula, et al.

It is certified that error appears in the above-indentified patent and that said Letters Patent is hereby corrected as shown below:

On the title page, item [54] and col. 1, line 1:

IN THE TITLE:

Please delete "HIGH MOTECULAR WEIGHT LINKED ESTERIFIED PROPOXYLATED GLYCERINS USEFUL AS GELLING OR THICKENING AGENTS" and insert in its place --HIGH MOLECULAR WEIGHT LINKED ESTERIFIED PROPOXYLATED GLYCERINS USEFUL AS GELLING OR THICKENING AGENTS--.

Signed and Sealed this

Sixteenth Day of July, 1996

Attest:

BRUCE LEHMAN

Attesting Officer                Commissioner of Patents and Trademarks